United States Patent
Zou et al.

(10) Patent No.: US 9,128,194 B2
(45) Date of Patent: Sep. 8, 2015

(54) PILEUP CORRECTION METHOD FOR A PHOTON-COUNTING DETECTOR

(71) Applicants: Kabushiki Kaisha Toshiba, Minato-ku (JP); Toshiba Medical Systems Corporation, Otawara-shi (JP)

(72) Inventors: Yu Zou, Naperville, IL (US); Xiaolan Wang, Buffalo Grove, IL (US); Chunguang Cao, Buffalo Grove, IL (US); Miesher L. Rodrigues, Buffalo Grove, IL (US); Yuexing Zhang, Naperville, IL (US); Daniel Gagnon, Twinsburg, OH (US)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 260 days.

(21) Appl. No.: 13/866,695

(22) Filed: Apr. 19, 2013

(65) Prior Publication Data

US 2014/0314211 A1 Oct. 23, 2014

(51) Int. Cl.
*G01T 1/17* (2006.01)

(52) U.S. Cl.
CPC .................................. *G01T 1/171* (2013.01)

(58) Field of Classification Search
CPC ...................................................... G01T 1/171
USPC ............ 378/19, 98.8, 207; 250/252.1, 370.09
See application file for complete search history.

(56) References Cited

U.S. PATENT DOCUMENTS 5,349,193 A * 9/1994 Mott et al. ................ 250/370.06
6,297,506 B1 * 10/2001 Young et al. .................. 250/369
(Continued)

FOREIGN PATENT DOCUMENTS

JP 2005-172823 A 6/2005
JP 2009-513220 A 4/2009
(Continued)

OTHER PUBLICATIONS

Katsuyuki Taguchi et al., "An analytical model of the effects of pulse pileup on the energy spectrum recorded by energy resolved photon counting x-ray detectors," Med. Phys. 37 (8), Aug. 2010, 3957-3969.*

(Continued)

*Primary Examiner* — Allen C. Ho
(74) *Attorney, Agent, or Firm* — Oblon, McClelland, Maier & Neustadt, L.L.P.

(57) ABSTRACT

A method and apparatus for determining a parameter vector that includes a plurality of parameters of a detector pileup model of a photon-counting detector, the detector pileup model being used for pileup correction for a spectral computed-tomography scanner. The method includes setting values of the parameters, the parameters including a dead time parameter and individual probabilities of different pileup events, the probabilities including a probability of single photon events, a probability of double quasi-coincident photon events, and a probability of at least three quasi-coincident photon events. The method include determining, using (1) a detector response model, (2) an incident spectrum, and (3) the set values of the parameter vector, a plurality of component spectra, each component spectrum corresponding to one of the individual probabilities of the different pileup events, and summing the plurality of component spectra to generate an output spectrum.

19 Claims, 7 Drawing Sheets (56) References Cited

U.S. PATENT DOCUMENTS

| | | | |
|---|---|---|---|
| 6,310,349 B1 * | 10/2001 | Wong et al. | 250/363.09 |
| 6,590,957 B1 * | 7/2003 | Grudberg et al. | 378/91 |
| 6,609,075 B1 * | 8/2003 | Warburton et al. | 702/87 |
| 6,917,041 B2 * | 7/2005 | Doty et al. | 250/370.09 |
| 6,936,822 B2 * | 8/2005 | Wong et al. | 250/363.09 |
| 7,170,065 B2 * | 1/2007 | Dagan et al. | 250/370.12 |
| 7,263,167 B2 * | 8/2007 | Walter et al. | 378/116 |
| 7,268,354 B2 * | 9/2007 | Heismann et al. | 250/395 |
| 7,480,362 B2 * | 1/2009 | Carmi | 378/19 |
| 7,966,155 B2 * | 6/2011 | Warburton et al. | 702/190 |
| 8,704,186 B2 * | 4/2014 | Nelson et al. | 250/370.06 |
| 8,812,268 B2 * | 8/2014 | Scoullar et al. | 702/189 |
| 2005/0123090 A1 | 6/2005 | Heismann et al. | |
| 2007/0076848 A1 | 4/2007 | Walter et al. | |
| 2008/0260094 A1 | 10/2008 | Carmi | |

FOREIGN PATENT DOCUMENTS

| | | |
|---|---|---|
| JP | 2012-187143 A | 10/2012 |
| JP | 2013-39306 A | 2/2013 |
| JP | 2013-192951 A | 9/2013 |
| WO | WO 2007/049168 A2 | 5/2007 |

OTHER PUBLICATIONS

International Search Report and Written Opinion issued Jul. 22, 2014 in PCT/JP2014/061057 (with English translation of categories).

Katsuyuki Taguchi, et al., "An analytical model of the effects of pulse pileup on the energy spectrum recorded by energy resolved photon counting x-ray detectors" Medical Physics, vol. 37, No. 8, Aug. 2010, pp. 3957-3969 and cover pages.

M. Kafaee, et al., "Pile-up correction by Genetic Algorithm and Artificial Neural Network" Nuclear Instruments and Methods in Physics Research Section A, vol. 607, No. 3, 2009, pp. 652-658 and cover pages.

* cited by examiner

FIG. 7

PILEUP CORRECTION METHOD FOR A PHOTON-COUNTING DETECTOR

FIELD

Embodiments disclosed herein generally relate to pile-up correction for photon-counting detectors in a spectral computed tomography (CT) system.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed. In the reconstruction, the map of the linear attenuation coefficient (LAC) of the imaged subjects is obtained from the line integrals of the LAC through an inverse Radon transform. The line integrals can be related to the logarithm of the primary intensity of the X-rays passing through the subject. However, the measured X-ray intensity on the detector may include both scattering photons and primary photons. Thus, the images reconstructed from scattering, contaminated intensities may contain some scattering artifacts.

A third-generation CT system can include sparsely distributed fourth-generation, photon-counting detectors. In such a combined system, the fourth-generation detectors collect primary beams through a range of detector fan angles.

Many clinical applications can benefit from spectral CT technology, which can provide improvement in material differentiation and beam hardening correction. Further, semiconductor-based photon-counting detectors are a promising candidate for spectral CT, which is capable of providing better spectral information compared with conventional spectral CT technology (e.g., dual-source, kVp-switching, etc.).

Due to the dead time (~100 ns), which is determined by the type of semiconductor (e.g. CZT or Cd Te), its thickness and readout circuit, pulse pileup at high X-ray flux (~$10^8$ cps/mm$^2$) can be very severe, and the measured spectral signals can be distorted. The distorted spectral signal can cause artifacts in the reconstruction images. Furthermore, the dead time is not a constant for a given readout circuit due to the location of the pulse formation within the detector cell. However, if the pileup effect can be corrected in the detector model, the image quality can be improved.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Embodiments described herein are directed to a new system and method for pileup modeling and correction for fourth-generation spectral, photon-counting CT detectors.

According to one embodiment, there is provided a method for determining a parameter vector that includes a plurality of parameters of a detector pileup model of a photon-counting detector, the detector pileup model being used for pileup correction for a spectral computed-tomography scanner, the method comprising: (1) setting values of the plurality of parameters, the parameters including a dead time parameter and individual probabilities of different pileup events, the probabilities including a probability of single photon events, a probability of double quasi-coincident photon events, and a probability of at least three quasi-coincident photon events; (2) determining, using (a) a detector response model, (b) an incident spectrum, and (c) the set values of the parameter vector, a plurality of component spectra, each component spectrum corresponding to one of the individual probabilities of the different pileup events; (3) summing the plurality of component spectra to generate an output spectrum; (4) calculating, based on the output spectrum and a measured spectrum, a value of a cost function; (5) updating at least one of the values of the parameter vector; and (6) repeating the determining, summing, calculating, and updating steps until a stopping criteria is met, so as to determine a parameter vector that optimizes the cost function.

In one embodiment, the setting step comprises setting the dead time parameter based on the scanner geometry.

In another embodiment the calculating step comprises calculating the value of the cost function using:

$$\psi^2(\underline{a}) = \int dE [S_{out}(E,\underline{a}) - S_m(E)]^2$$

wherein $\psi(\underline{a})$ is the cost function, $\underline{a}$ is the parameter vector, $S_{out}(E;\underline{a})$ is the output spectrum, $Sm(E)$ is the measured spectrum, and E is energy.

In another embodiment, the parameters further include a time threshold to distinguish between peak pileup events and tail pileup events, and the determining step comprises determining, for the double quasi-coincident photon events, a peak pileup component spectrum and a tail pileup component spectrum.

In another embodiment, the repeating step comprises repeating the determining, summing, calculating, and updating steps until the cost function falls below a predetermined threshold or for a predetermined number of iterations.

In another embodiment, the updating step comprises updating the parameter vector a according to an exhaustive search method.

In another embodiment, the updating step comprises updating the parameter vector a according to a nonlinear least-squares method.

In another embodiment, the determining step comprises determining, as one of the plurality of component spectra, a first component spectrum for single photon events, the first component spectrum being determined as:

$$S_0(E) = e^{-n\tau_d} \int dz_0 dE_0 \chi_0 S_{in}(E_0) e^{-\mu_{CZT}(E_0)z_0} \mu_{CZT}(E_0)$$

where $S_{in}$ is the incident spectrum, n is an incident count rate, $\mu_{CZT}(E)$ is a linear attenuation value, z is depth, and $\tau_d$ is the dead time parameter.

In another embodiment, there is provided a method of performing pileup correction for a spectral computed-tomography scanner, the scanner including a photon-counting detector, the method comprising (1) determining, using the method described above, a parameter vector that includes a plurality of parameters of a detector pileup model of the photon-counting detector; (2) performing a scan using the scanner to generate a measured spectrum for the photon-counting detector; and (3) determining, using the detector pileup model and the measured spectrum, an incident spectrum for the photon-counting detector.

In another embodiment, there is provided a device for determining a parameter vector that includes a plurality of parameters of a detector pileup model of a photon-counting detector, the detector pileup model being used for pileup correction for a spectral computed-tomography scanner, the device comprising a processor configured to (1) set values of the plurality of parameters, the parameters including a dead time parameter and individual probabilities of different pileup events, the probabilities including a probability of single photon events, a probability of double quasi-coincident photon events, and a probability of at least three quasi-coincident photon events; (2) determine, using (a) a detector response model, (b) an incident spectrum, and (c) the set values of the parameter vector, a plurality of component spectra, each component spectrum corresponding to one of the individual probabilities of the different pileup events; (3) sum the plurality of component spectra to generate an output spectrum; (4) calculate, based on the output spectrum and a measured spectrum, a value of a cost function; (5) update at least one of the values of the parameter vector; and (6) repeat the determining, summing, calculating, and updating steps until a stopping criteria is met, so as to determine a parameter vector that optimizes the cost function.

In another embodiment, there is provided a method for determining an output spectrum from a parameter vector that includes a plurality of parameters of a detector pileup model of a photon-counting detector, the detector pileup model being used for pileup correction for a spectral computed-tomography scanner, the method comprising: (1) setting values of the plurality of parameters, the parameters including a dead time parameter and individual probabilities of different pileup events, the probabilities including a probability of single photon events and a probability of double quasi-coincident photon events; (2) determining, using (a) a detector response model, (b) an incident spectrum, and (c) the set values of the parameter vector, a plurality of component spectra, each component spectrum corresponding to one of the individual probabilities of the different pileup events, wherein the determining step includes determining, as one of the plurality of component spectra, a first component spectrum for single photon events, the first component spectrum being determined as:

$$S_0(E) = e^{-n\tau_d} \iint dz_0 dE_0 \chi_0 S_{in}(E_0) e^{-\mu_{CZT}(E_0)z_0} \mu_{CZT}(E_0)$$

where $S_0(E)$ is determined from the detected energy, E, which is defined as $$E = \nu_p(t_{TOF}^0; z_0, E_0),$$

$S_{in}$ is the incident spectrum, $E_0$ is the incident energy, $z_0$ is an interaction point, n is an incident count rate, $\mu_{CZT}(E)$ is a linear attenuation value, $\tau_d$ is the dead time parameter, $\nu_p$ is an output voltage of a pre-amplifier; and $\chi_0$ is a probability of single photon events; and (3) summing the plurality of component spectra to generate the output spectrum.

Figure 1:
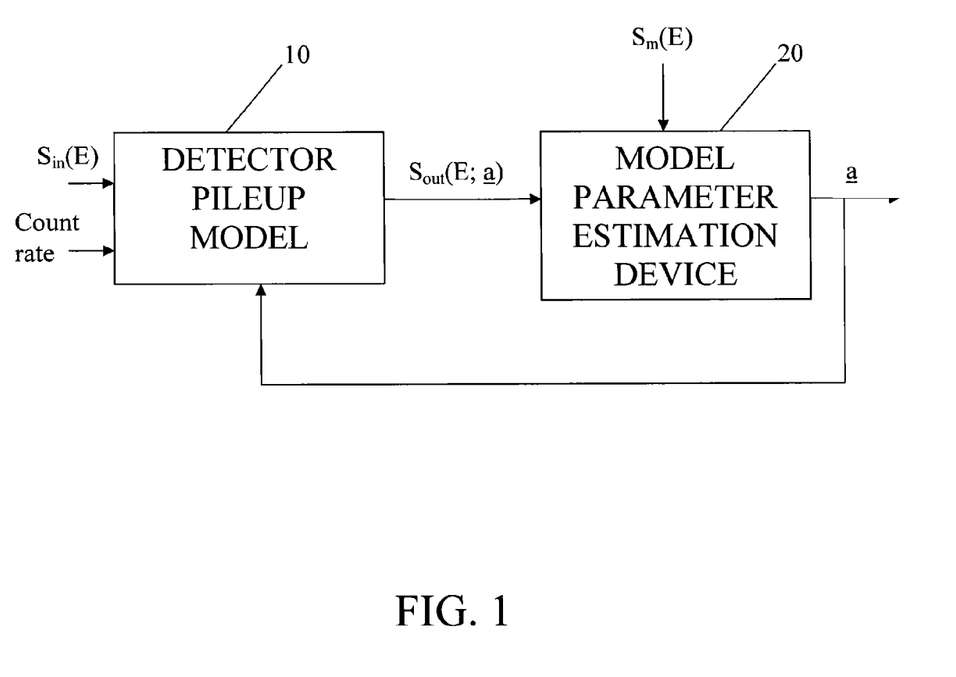
FIG. 1 illustrates an apparatus for determining a detector pileup model for a photon-counting detector.

Turning now to the drawings, FIG. 1 illustrates an apparatus for determining a detector pileup model for each photon-counting detector in a spectral CT scanner. In particular, FIG. 1 illustrates a detector pileup model 10 that receives an incident spectrum $S_{in}(E)$, a count rate, and a parameter vector $\underline{a}$. Based on the received values, the detector pileup model 10 generates a simulated measured spectrum $S_{out}(E; \underline{a})$. The process of determining the simulated measured spectrum $S_{out}(E; \underline{a})$ will be described in more detail below.

As shown in FIG. 1, the model parameter estimation device 20 compares the simulated measured spectrum $S_{out}(E; \underline{a})$ with an actual measured spectrum $S_m(E)$, and updates the parameter vector $\underline{a}$ so as to minimize a predetermined cost function. The updated parameter vector $\underline{a}$ is fed back to the detector pileup model 10 to generate a new simulated measured spectrum $S_{out}(E; \underline{a})$. This process continues for a predetermined number of iterations or until the change in the parameter vector $\underline{a}$ falls below a predetermined threshold. As described below, the model parameter estimation device 20 can employ, e.g., an exhaustive search within a predefined range for the parameter vector $\underline{a}$, or a nonlinear least-squares method for finding the optimal parameter vector $\underline{a}$. A respective optimal parameter $\underline{a}$ is found for each photon-counting detector (PCD) in a scanner.

The incident spectrum $S_{in}(E)$ can be determined by calculation (all vendors have models to calculate the output from their tubes) or measurements (by using a gold-standard spectroscopic detector, e.g., a high-purity germanium spectrometer) for each PCD in a scanner. The measured spectrum $S_m(E)$ is the output spectrum from each PCD corresponding to each incident spectrum $S_{in}(E)$.

The parameter vector $\underline{a}$ includes a dead time value $\tau_d$, a time threshold T to determine whether, e.g., double photon events are peak pileup events or tail pileup events (although threshold this applies to determining whether a peak or tail pileup event occurs at any pileup order), and individual probabilities of different number of quasi-coincident photons $\chi_0$, $\chi_1^P$, $\chi_1^t$, $\chi_2^P$, $\chi_2^t$, etc. For example, $\chi_0$ is the probability of single photon events, $\chi_1^P$ is the probability of peak double pileup events, $\chi_1^t$ is the probability of tail double pileup events, $\chi_2^P$ is the probability of triple peak pileup events, etc. Note that, in practice, the contribution of higher order spectra drops quickly with increasing order and, in most embodiments, those spectra can be ignored in calculating the summed spectrum. Note that the sum of individual probabilities will be equal to or less than 1.

Figure 2:
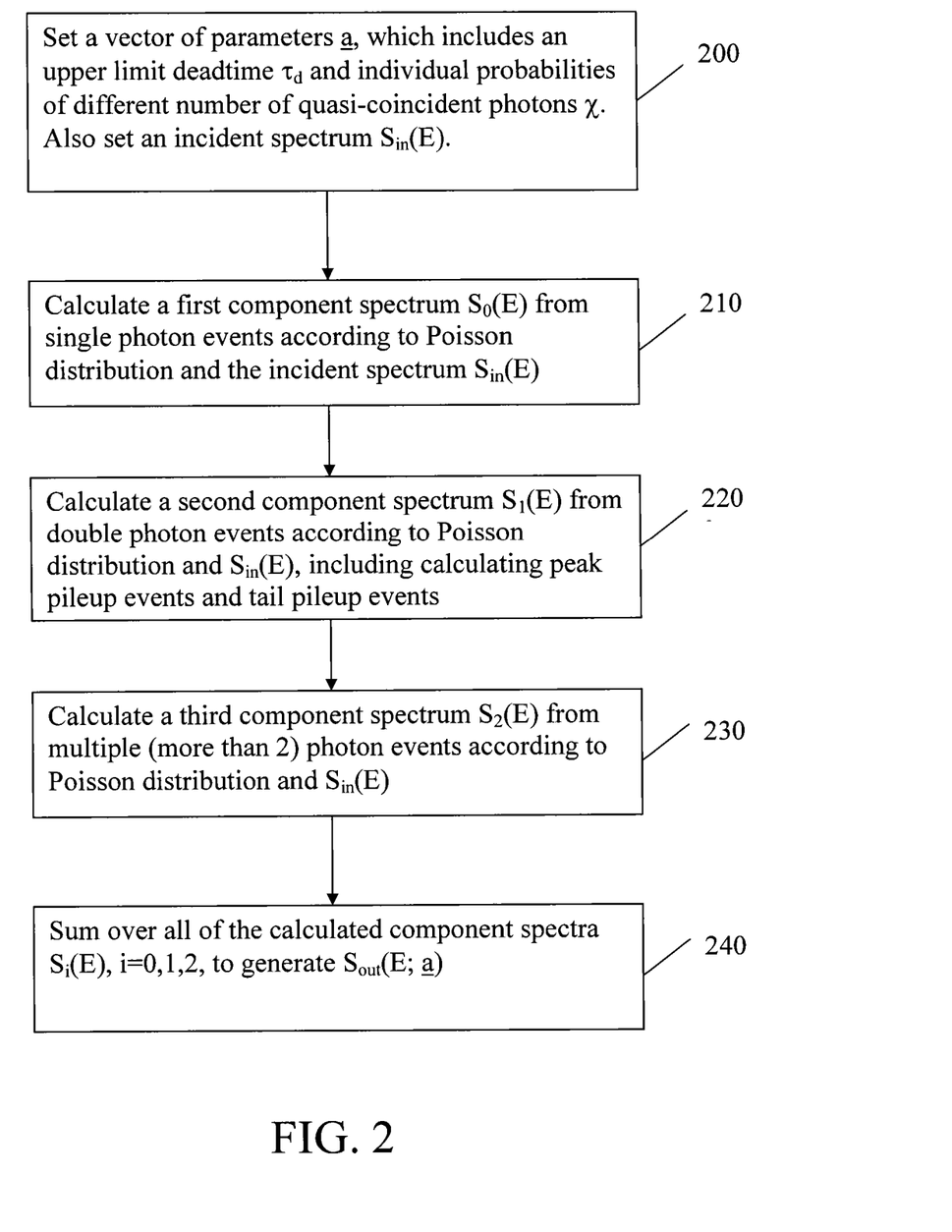
FIG. 2 illustrates a method for determining an output of a detector pileup model for a photon-counting detector.

The detector pileup model 10 computes $S_{out}(E; \underline{a})$ from $S_{in}(E)$ and the parameter a using the method illustrated in FIG. 2.

In particular, in step 200, the parameter vector $\underline{a}$ and the incident spectrum $S_{in}(E)$ are received or set.

In step 210, a first component spectrum $S_0(E)$ is calculated using $S_{in}(E)$ and the parameter vector $\underline{a}$. A Poisson distribution is assumed for the single photon events and the effects of pixel weighting potential, depth of interaction, ballistic deficit, and space charge are included in the calculation of $S_1(E)$. Note that the use of the Poisson distribution is reflected in the terms $e^{-n\tau_d}$, $ne^{-n\tau_d}$, $\frac{1}{2}n^2 e^{-n\tau_d}$, etc. of the component spectra equations (S0, S1, S2, etc.) shown below.

In particular, the weighting potential is defined as follows:

$$w(z) = \frac{z}{L} - \frac{\alpha \sin \pi z}{L}, \quad 0 \le z \le L$$

-continued $$z = \begin{cases} z_0, t < 0 \\ v_\theta t + z_0, 0 \le t \le t_{TOF} = \dfrac{L-z_0}{v_\theta} \\ L, t > t_{TOF} \end{cases}$$

where z indicates the distance between a point in CZT and the cathode, $z_0$ is the point where an X-ray photon converts to electron-hole pairs, $t_{TOF}$ is the time for the generated electrons to drift from the interaction point $z_0$ to the anode of the detector. Also, $\alpha$ is a model parameter describing the weighting potential distribution of the detector, L is the detector thickness, and $v_e$ is the drifting velocity of the electron carriers in the photon-counting detector.

For ballistic deficit, the basic equations are:

$$\tau_p \frac{dv_p(t)}{dt} + v_p(t) = \tau_p \frac{dv_{in}(t)}{dt}$$

$$v_{in}(t) = KE[w(z(t)) - w(z_0)]$$

where E is the incident energy, and K is the front-end gain (a constant for a given readout configuration), $\tau_p$ is the time constant of the pre-amplifier, and $v_p(t)$ is the output voltage of the pre-amplifier.

For $0 \le t \le t_{TOF}$ from the basic equations, the pre-amplifier output can be written as:

$$v_p(t) = e^{-\frac{t}{\tau_p}} \left[ \int dt KE \frac{dz(t)}{dt} \frac{dw(z)}{dz} e^{\frac{t}{\tau_p}} + v^0 \right]$$

where $v^0$ is determined by the initial condition, $$v_p(0) = 0.$$

Inserting the weighting potential equations into above equation, we have, $$v_p(t) = e^{-\frac{t}{\tau_p}} \left[ \int dt KE v_\theta \left( \frac{\frac{1}{L} - \alpha \frac{\pi}{L} \cos(\pi(v_\theta t + z_0))}{L} \right) e^{\frac{t}{\tau_p}} + v^0 \right].$$

Calculating the integration, we have $$v_p(t) = e^{-\frac{t}{\tau_p}}$$

$$\left[ KEv_\theta \left( \frac{\tau_p}{L} - \alpha \frac{\pi}{L} \frac{\frac{1}{\tau_p}\cos(\pi(v_\theta t + z_0)) + \frac{\pi v_\theta}{L}\sin(\pi(v_\theta t + z_0))}{L \left( \left(\frac{\pi v_\theta}{L}\right)^2 + \left(\frac{1}{\tau_p}\right)^2 \right)} \right) e^{\frac{t}{\tau_p}} + v^0 \right].$$

Applying the initial condition, the constant $v^0$ can be expressed as, $$v^0 = -\frac{KE\tau_p}{\tau_{TOF}} \left( 1 - \frac{\alpha\pi \left( \frac{\cos(\pi z_O)}{L} + \frac{\pi\tau_p}{\tau_{TOF}} \sin(\pi z_0) \right)}{\left( \frac{\pi\tau_p}{\tau_{TOF}} \right)^2 + 1} \right).$$

where $$\tau_{TOF} = \frac{L}{v_\theta}.$$

$$v^0 = -\frac{KE\tau_p}{\tau_{TOF}} \left( 1 - \frac{\alpha\pi \left( \frac{\cos(\pi z_O)}{L} + \frac{\pi\tau_p}{\tau_{TOF}} \sin(\pi z_0) \right)}{\left( \frac{\pi\tau_p}{\tau_{TOF}} \right)^2 + 1} \right)$$

At $$t_{TOF} = \frac{L - z_0}{v_\theta},$$

the generated electron will reach the anode of the detector. Accordingly, the pre-amplifier output reaches the maximum, $$v_p(t_{TOF}) = \frac{KE\tau_p}{\tau_{TOF}} \left( 1 - \frac{\alpha\pi}{\left(\frac{\pi\tau_p}{\tau_{TOF}}\right)^2 + 1} \right) + v^0 e^{-\frac{t_{TOF}}{\tau_p}}.$$

$$t_{TOF} = \frac{L - z_0}{v_\theta}$$

Note that $t_{TOF}$ will be different if space charge becomes non-negligible.

For the case $t > t_{TOF}$ after $t_{TOF}$ the signal collection is complete and the output amplitude decays exponentially with the front-end circuitry time constant, $\tau_p$.

$$v_p(t) = v_p(t_{TOF}) e^{-\frac{t - t_{TOF}}{\tau_p}}$$

As illustrated above, the formulation of $v_p(t)$ depends on depth of interaction, $z_0$ and the incident energy, $E_0$. Therefore, we will denote it as $v_p(t) = v_p(t:z_0,E_0)$. Below, for ease of representation, we may omit $E_0$ in $v_p(t)$. Below, we also use $\{t_{TOF}{}^j : z_j\}$ to define the time-of-flight and depth-of-interaction of event j, respectively.

For the no pileup case, the first component spectrum is calculated as follows. First, the detected energy, E, is defined as $$E = v_p(t_{TOF}{}^0 : z_0, E_0).$$

Next, the component spectrum becomes:

$$S_0(E) = e^{-n\tau_d} \iint dz_0 dE_0 \chi_0 S_{in}(E_0) e^{-\mu_{CZT}(E_0)z_0} \mu_{CZT}(E_0)$$

where the integration runs over the whole volume with the energy condition. Note that detection probability $\chi_0 \sim 1$ if the flexible dead time close to true dead time. In the above equation, n is the incident count rate and $\mu_{CZT}(E)$ is the linear attenuation of CZT at energy E.

In step 220, a second component spectrum $S_1(E)$ for double photon events including peak pileup events and tail pileup events is calculated using $S_{in}(E)$ and the parameter vector $\underline{a}$. For double photon events, a peak pileup event is determined to have occurred when the time interval between events is smaller than a threshold T, and a tail pileup event is determined to have occurred when the time interval is larger than the threshold T. The threshold T is included in the model parameter vector $\underline{a}$.

In particular, for peak pileup events, the energy is defined as:

$$E = v_p(t_{TOF}^0; z_0)e^{-\frac{t_{max}-t_{TOF}^0}{\tau_p}} + v_p(t_{TOF}^1; z_1)e^{-\frac{t_{max}-t_{TOF}^1-t_1}{\tau_p}}$$

$$[t_{max} = \max(t)_1 + t_{TOF}^1, t_{TOF}^0)$$

Then the peak component spectrum becomes:

$$S_1^P(E) = ne^{-n\tau d}\iiiii dz_0 dE_0 dt_1 dz_1 dE_1 \chi_1^P S_{in}(E_0) S_{in}(E_1) e^{-\mu_{CZT}(E_0)z_0 - \mu_{CZT}(E_1)z_1} \mu_{CZT}(E_0) \mu_{CZT}(E_1)$$

Note that detection probability $\chi_1^P \sim 1/2$, if the flexible dead time close to the true dead time.

For tail pileup, the first peak energy is defined as:

$$E^0 = v_p(t_{TOF}^0; z_0) + v_p(t_{TOF}^0 - t_1; z_1)$$

Then, the component spectrum becomes:

$$S_1^{t0}(E) = ne^{-n\tau d}\iiiii dz_0 dE_0 dt_1 dz_1 dE_1 \chi_1^{t0} S_{in}(E_0) S_{in}(E_1)$$
$$e^{-\mu_{CZT}(E_0)z_0 - \mu_{CZT}(E_1)z_1} \mu_{CZT}(E_0) \mu_{CZT}(E_1)$$

Further, the second peak energy is defined as:

$$E^1 = v_p(t_{TOF}^1 + t_1; z_0) + v_p(t_{TOF}^1; z_1)$$

Then the component spectrum becomes:

$$S_1^{t1}(E) = ne^{-n\tau d}\iiiii dz_0 dE_0 dt_1 dz_1 dE_1 \chi_1^{t1} S_{in}(E_0) S_{in}(E_1)$$
$$e^{-\mu_{CZT}(E_0)z_0 - \mu_{CZT}(E_1)z_1} \mu_{CZT}(E_0) \mu_{CZT}(E_1)$$

Note that detection probability $\chi_1^{t0} \sim 0, \chi_1^{t1} \sim 0$ if the flexible dead time is close to the true dead time. The peak and tail pileup component spectrum are added to form $S_1(E)$.

In step 230, a third component spectrum $S_2(E)$ for multiple photon events including peak pileup events and tail pileup events is calculated using $S_{in}(E)$ and the parameter vector $\underline{a}$.

In particular, in the triple pileup case, for peak pileup, the energy is defined as:

$$E = v_p(t_{TOF}^0; z_0)e^{-\frac{t_{max}-t_{TOF}^0}{\tau_p}} + $$
$$v_p(t_{TOF}^1; z_1)e^{-\frac{t_{max}-t_{TOF}^1-t_1}{\tau_p}} + v_p(t_{TOF}^2; z_2)e^{-\frac{t_{max}-t_{TOF}^2-t_2}{\tau_p}}$$

$$t_{max} = \max(t_2 + t_{TOF}^2, t_1 + t_{TOF}^1, t_{TOF}^0)$$

Then, the peak component spectrum becomes:

$$S_2^P(E) = \tfrac{1}{2}n^2 e^{-n\tau d}\iiiiiii dz_0 dE_0 dt_1 dz_1 dE_1 dt_2 dz_2 dE_2 \chi_2^P S_{in}(E_0) S_{in}(E_1) S_{in}(E_2) \times e^{-\mu_{CZT}(E_0)z_0 - \mu_{CZT}(E_1)z_1 - \mu_{CZT}(E_2)z_2} \mu_{CZT}(E_0) \mu_{CZT}(E_1) \mu_{CZT}(E_2)$$

Note that detection probability $\chi_2^P \sim 1/3$ if the flexible dead time close to the true dead time. As an approximation:

$$S_2^P(E) \approx \tfrac{1}{2}n^2 e^{-n\tau d}\iiint dE' dz_2 dE_2 \chi_2^P S_{norm}(E') S_{in}(E_2) e^{-\mu_{CZT}(E_2)z_2} \mu_{CZT}(E_2)$$

where, $S_{norm}(E) = N[S_0(E) + S_1^P(E) + S_1^{t0}(E) + S_1^{t1}(E)]$, where N is a normalization factor.

For the tail pileup case or the mixed tail-peak pileup case, the calculation is similar to that of double pileup, but there are more combinations to consider. For example, for a first combination (0-1-2), the energy is defined as:

$$E^0 = v_p(t_{TOF}^0; z_0) + v_p(t_{TOF}^0 - t_1; z_1) + v_p(t_{TOF}^0 - t_2; z_2)$$

$$E^1 = v_p(t_{TOF}^1 + t_1; z_0) + v_p(t_{TOF}^1; z_1) + v_p(t_{TOF}^1 - t_2; z_2)$$

$$E^2 = v_p(t_{TOF}^2 + t_2; z_0) + v_p(t_{TOF}^2 + t_2 - t_1; z_1) + \sigma_p(t_{TOF}^2; z_2)$$

For a second combination ((01)-2), the energy is defined as:

$$E^{01} = v_p(t_{max}; z_0) + v_p(t_{max} - t_1; z_1) + v_p(t_{max} - t_2; z_2)$$

$$[t_{max} = \max(t)_1 + t_{TOF}^1, t_{TOF}^0)$$

$$E^2 = v_p(t_{TOF}^2; z_0) + v_p(t_{TOF}^2 + t_2 - t_1; z_1) + v_p(t_{TOF}^2; z_2)$$

Other combinations, such as ((02)-1) and ((12)-0) are similar to the second combination set forth above.

For the tail pileup case or the mixed tail-peak pileup case, the corresponding formula can be obtained readily by generalizing the formula used for double pileup. In one embodiment, an approximation for peak pileup is used and the tail pileup is ignored.

In an alternative embodiment, triple photon events are treated as a double event between (1) a double event (first-order pileup) and a single event (no pileup). In this case, the component spectrum is calculated from a double-event component spectrum and a no-pileup component spectrum. One component spectrum will replace one term $S_{in}(E)$ in the double-event equation $S_1(E)$ shown above, while the other component spectrum will replace the other $S_{in}(E)$ in the same equation. This approach can be extended to higher-order pileup events.

Figure 4:
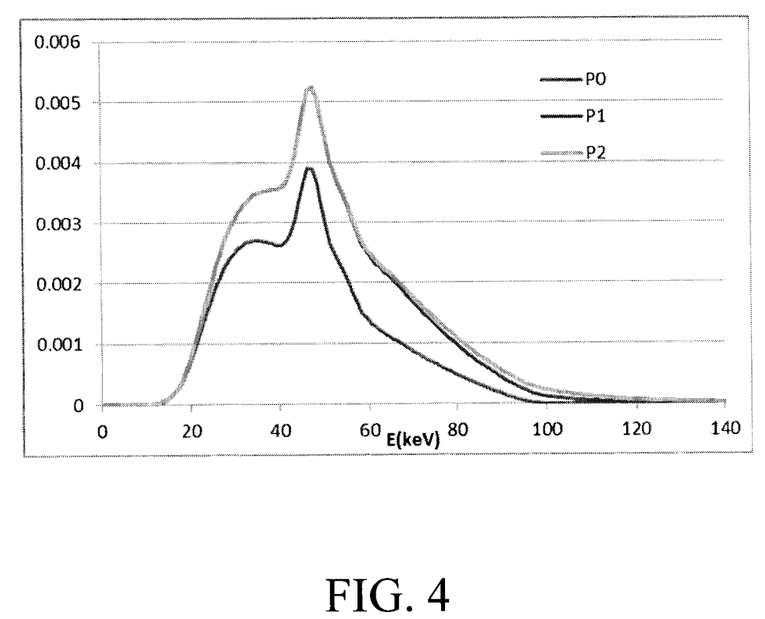
FIGS. 4 and 5 illustrate simulated component spectra using a detector pileup model.

In step 240, the calculated component spectra $S_i(E)$, i=0, 1, 2, etc. are summed to generate $S_{out}(E; \underline{a})$. FIG. 4 illustrates partial summation of the component spectra described above. In particular, P0 is the single photon event spectrum $S_0(E)$, while P1 is the sum of the first and second component spectra $S_0(E) + S_1(E)$. Finally, P2 is the sum of the first, second, and third component spectra, which in this example, equals $S_{out}(E; \underline{a})$.

Figure 5:
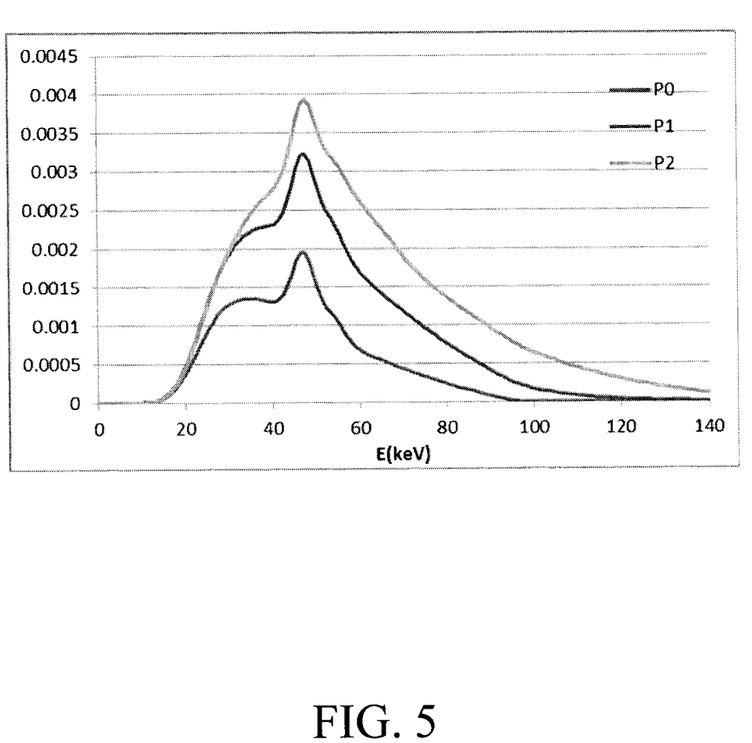

By comparison, FIG. 5 shows partial summation of the component spectra calculated with constant values for the detection probabilities. Note that with constant detection probabilities the pileup effect is overestimated.

Figure 3:
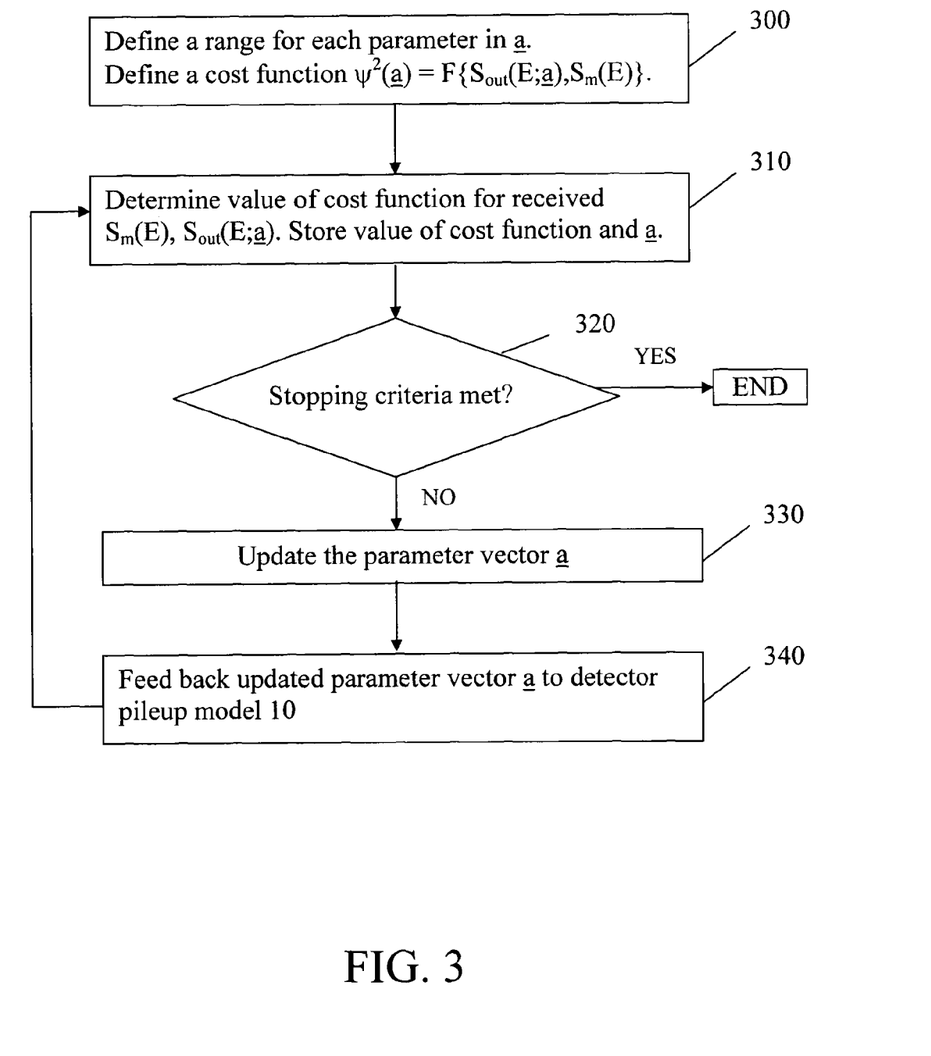
FIG. 3 illustrates a method performed by a pileup model parameter estimation device.

As noted above, the model parameter estimation device 20 shown in FIG. 1 compares the simulated measured spectrum $S_{out}(E; \underline{a})$ with an actual measured spectrum $S_m(E)$, and updates the parameter vector $\underline{a}$ so as to minimize a predetermined cost function. The method used to find the optimal parameter values $\underline{a}$ is shown in FIG. 3.

In particular, in step 300, suitable ranges for each of the parameters in the parameter vector a are defined and a cost function $\psi(\underline{a})$ is defined, e.g., as:

$$\psi^2(\underline{a}) = \int dE [S_{out}(E; \underline{a}) - S_m(E)]^2$$

Other suitable cost functions can be used.

In step 310, the value of the cost function is calculated based on received values of $S_{out}(E; \underline{a})$ and the measured spectrum $S_m(E)$. Further, the calculated value of the cost function $\psi(\underline{a})$ is stored in association with the current parameter vector $\underline{a}$.

In step 320, the stopping criteria are checked. For example, a change in the parameter vector $\underline{a}$ is determined and if the change in the parameter vector $\underline{a}$ falls below a predetermined threshold, the process ends. Otherwise, the process continues to step 330. Alternatively, the process can end when the number of iterations exceeds a predetermined number. Other combinations of stopping criteria can be used, such as stopping when the number of iterations exceeds a predetermined number or the change in the parameter vector $\underline{a}$ falls below a predetermined threshold.

In step 330, depending on the particular optimization method used, the parameter vector $\underline{a}$ is updated. For example, if an exhaustive search algorithm is being used, the vector $\underline{a}$ is updated in a predetermined systematic manner within the range defined for each parameter. Alternatively, a nonlinear least-squares fitting method, such as Levenberg-Marquardt, can be used. In that method, gradients of the cost function are estimated. Other optimization methods can be used to minimize the cost function.

In step 340, the updated parameter vector $\underline{a}$ is fed back to the detector pileup model 10, which calculates a new $S_{out}(E; \underline{a})$ using the updated parameter vector $\underline{a}$. The process then proceeds to step 310, in which the new $S_{out}(E; \underline{a})$ values are received, and the cost function is computed again using the same measured spectrum $S_m(E)$.

In an alternative embodiment, one or more of the parameter values $\underline{a}$, such as the dead time $\tau_d$, can be derived directly from the detector geometry and the readout electronics configuration. Further, in another embodiment, a combination of the direct calculation approach and the empirical method described above with respect to FIGS. 1-3 is performed. For example, some of the parameter values $\underline{a}$ can be directly calculated and the remaining values can be determined empirically. Alternatively, initial estimates of the parameter values $\underline{a}$ can be calculated directly and used as the initial values in the empirical method described above, which reduces the computational load.

Once the optimal parameters of the detector pileup model are determined, as discussed above, various algorithms can be used for spectrum correction using the model, i.e., solving for the incident spectrum based on a measured spectrum. Examples include (1) gradient-based methods to minimize a cost function, (2) search-based methods to find the incident spectrum in a pre-determined search domain so as to minimize a cost function, and (3) response-function-based iterative methods.

In the response-function-based approach, the detector pileup model is defined or modeled as follows, for the linear case without pileup:

$$S_{out}(E) \approx \int dE' R(E,E') S_{in}(E')$$

where $R(E,E')$ is the response matrix of the detector model and incorporates the determined model parameters $\underline{a}$. From the component spectrum formula for no pileup, the response matrix can be defined as, $$R(E,E_0) = e^{-n\tau_d} \int dz_0 \chi_0 e^{-\mu_{CZT}(E_0)z_0} \mu_{CZT}(E_0)$$

The incident spectrum $S_{in}(E)$ is then obtained by solving the following equation iteratively:

$$S_{in}(E) = \frac{S_m(E) - \sum_{E'=E+1}^{E_{mas}} R(E, E') S_{in}(E')}{R(E, E)}$$

For the non-linear case with pileup, the detector model is defined as:

$$S_{out}(E) \approx \int dE' R(E,E') S_{in}(E') + \iint dE' dE'' R_2(E,E',E'') S_{in}(E') S_{in}(E'') + \ldots$$

Where $R_2(E,E',E'')$ is the double photon response matrix of the detector model and is determined using the model parameters $\underline{a}$. From the component spectrum formula for double peak pileup, the response matrix can be defined as, $$R_2^p(E,E_0,E_1) = ne^{-\tau_d} \iiint dz_0 dt_1 dz_1 \chi_1^p e^{-\mu_{CZT}(E_0)z_0 - \mu_{CZT}(E_1)z_1} \mu_{CZT}(E_0) \mu_{CZT}(E_1).$$

Similarly, we can define the double photon response matrix for tail pileup, $R_2^{r0}(E,E_0,E_1)$ and $R_2^{r1}(E,E_0,E_1)$. The total double photon response matrix can be expressed as, $$R_2^p(E,E_0,E_1) = R_2^p(E,E_0,E_1) + R_2^{r0}(E,E_0,E_1) + R_2^{r1}(E,E_0,E_1)$$

The incident spectrum $S_{in}(E)$ is then obtained by solving the following equation iteratively:

$$S_{in}(E) = \frac{S_m(E) - \iint dE' dE'' R_2(E,E',E'') S_{in}(E') S_{in}(E'') - \sum_{E'=E+1}^{E_{mas}} R(E,E') S_{in}(E')}{R(E,E)}$$

Note that these two equations can be readily extended to include a multiple (more than two) photon response matrix representing higher-order pileup.

The above-described embodiments for determining a detector pileup model have many advantages of conventional pileup correction methods. For example, the disclosed embodiments accommodate a flexible dead time, to handle the varying real dead time in a photon-counting detector, as well as a flexible pulse shape. Further, the disclosed embodiments include individual detection probabilities for different numbers of quasi-coincident photons, instead of the constant detection probability used in conventional approaches.

The model equations set forth above are based on particular weighting potential and ballistic deficit equations. These example weighting potential and ballistic deficit equations are used to illustrate only one example in which the calculation of $v_p(t)$ has a closed form. Other equations can be used and the component spectra can be similarly calculated (the probability method still holds), but with a different $v_p(t)$ function that may no longer have a closed-form solution.

Also, note that the pulse shape is incorporated in the weighting potential and ballistic deficit equations. Thus, a different pulse shape will result in different equations.

Moreover, the disclosed embodiments model realistic pixel weighting potential, depth of interaction, ballistic deficit, and space charge. The disclosed embodiments illustrate one example of weighting potential and a ballistic deficit model. However, in alternative embodiments, other models of signal induction and detector response, which are determined by the detector configuration, can be incorporated into the present methods.

Figure 6:
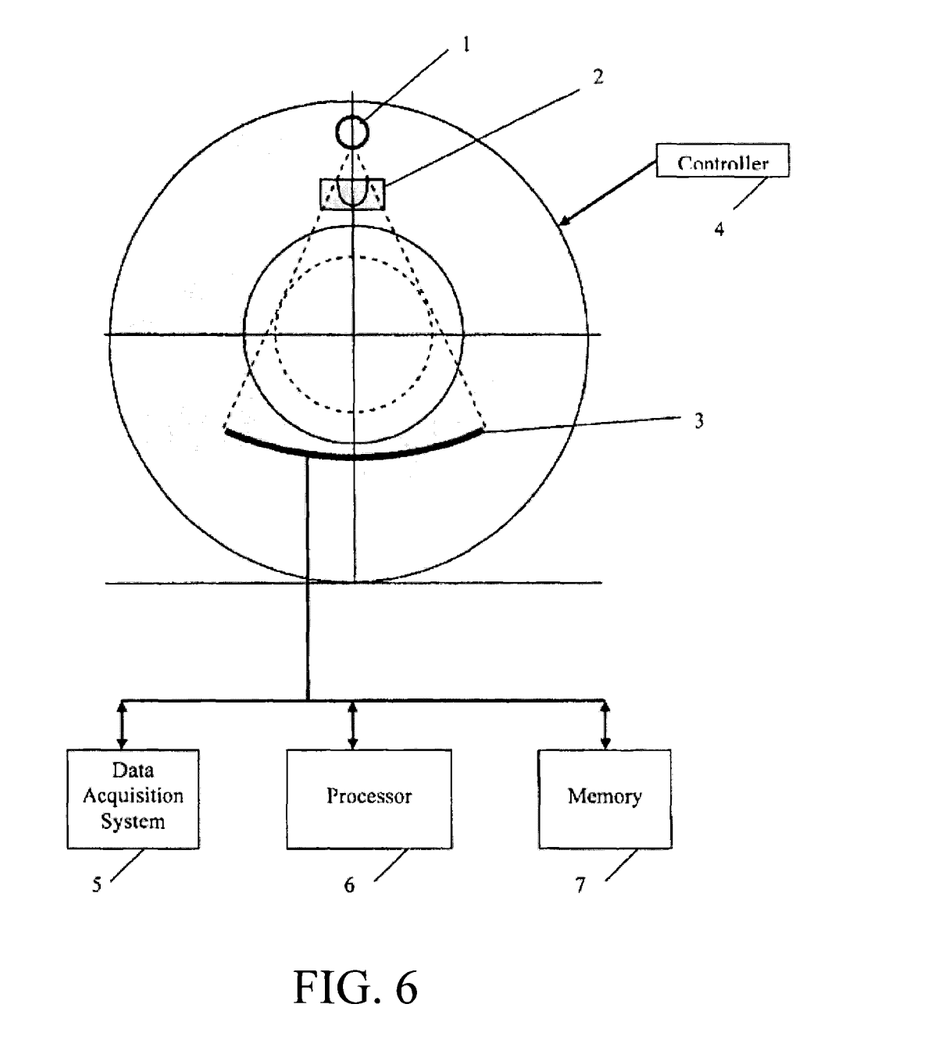
FIGS. 6 and 7 illustrate a CT scanner system according to the present embodiments.
Figure 7:
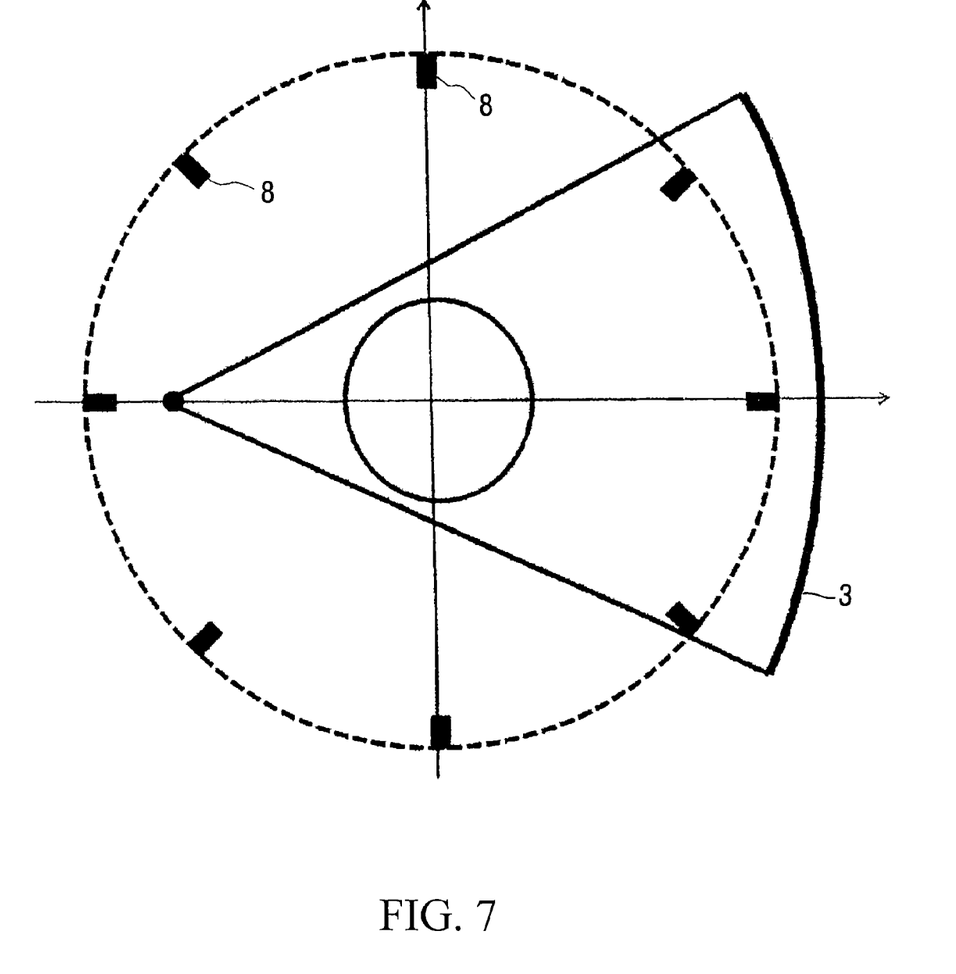

FIG. 6 illustrates the basic structure of a spectral CT scanner apparatus that includes the photon-counting detectors described herein. The CT apparatus of FIG. 6 includes an X-ray tube 1, filters and collimators 2, and third-generation detector 3. The CT apparatus also includes, e.g., sparse fixed energy-discriminating (e.g., photon-counting) detectors 8, which can be arranged at a different radius from that of the third-generation detector 3, as shown in FIG. 7. The CT apparatus will also include additional mechanical and electrical components, such as a gantry motor and a controller 4 to control the rotation of the gantry, control the X-ray tube 1, and control a patient bed. The CT apparatus also includes a data acquisition system 5 and a processor 6 to generate CT images based on the projection (view) data acquired by the data acquisition system. For example, the processor 6 included a reconstruction processor to reconstruct spectral CT images.

In particular, the processor 6 is programmed to perform methods for determining parameters of a detector pileup model and for performing pileup correction for each photon-counting detector, as described above. Further, the processor 6 and data acquisition system 5 make use of a memory 7, which is configured to store, e.g., computer programs, data obtained from the detector, the detector pileup models, and reconstructed images.

In one embodiment, the processor 6 is configured to set values of the plurality of parameters, the parameters including a dead time parameter and individual probabilities of different pileup events, the probabilities including a probability of single photon events, a probability of double quasi-coincident photon events, and a probability of at least three quasi-coincident photon events; determine, using (1) a detector response model, (2) an incident spectrum, and (3) the set values of the parameter vector, a plurality of component spectra, each component spectrum corresponding to one of the individual probabilities of the different pileup events; sum the plurality of component spectra to generate an output spectrum; calculate, based on the output spectrum and a measured spectrum, a value of a cost function; update at least one of the values of the parameter vector; and repeat the determining, summing, calculating, and updating steps until a stopping criteria is met, so as to determine a parameter vector that optimizes the cost function.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the pre-reconstruction processor, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for determining a parameter vector that includes a plurality of parameters of a detector pileup model of a photon-counting detector, the detector pileup model being used for pileup correction for a spectral computed-tomography scanner, the method comprising:

setting values of the plurality of parameters, the plurality of parameters including a dead time parameter and individual probabilities of different pileup events, the individual probabilities including a probability of single photon events, a probability of double quasi-coincident photon events, and a probability of at least three quasi-coincident photon events;

determining, using (1) a detector response model, (2) an incident spectrum, and (3) the set values of the parameter vector, a plurality of component spectra, each component spectrum corresponding to one of the individual probabilities of the different pileup events;

summing the plurality of component spectra to generate an output spectrum;

calculating, based on the output spectrum and a measured spectrum, a value of a cost function;

updating at least one of the values of the parameter vector; and repeating the determining, summing, calculating, and updating steps until a stopping criteria is met, so as to determine a parameter vector that optimizes the cost function.

2. The method of claim 1, wherein the setting step comprises setting the dead time parameter based on the scanner geometry.

3. The method of claim 1, wherein the calculating step comprises:

calculating the value of the cost function using:

$$\psi^2(\underline{a}) = \int dE [S_{out}(E,\underline{a}) - S_m(E)]^2$$

wherein $\psi(\underline{a})$ is the cost function, $\underline{a}$ is the parameter vector, is the output spectrum, $S_m(E)$ is the measured spectrum, and E is energy.

4. The method of claim 1, wherein the plurality of parameters further include a time threshold to distinguish between peak pileup events and tail pileup events; and the determining step comprises determining, for the double quasi-coincident photon events, a peak pileup component spectrum and a tail pileup component spectrum.

5. The method of claim 1, wherein the repeating step comprises repeating the determining, summing, calculating, and updating steps until the cost function falls below a predetermined threshold or for a predetermined number of iterations.

6. The method of claim 1, wherein the updating step comprises updating the parameter vector a according to an exhaustive search method.

7. The method of claim 1, wherein the updating step comprises updating the parameter vector a according to a nonlinear least-squares method.

8. The method of claim 1, wherein the determining step comprises:

determining, as one of the plurality of component spectra, a first component spectrum for single photon events, the first component spectrum being determined as:

$$S_0(E) = e^{-n\tau_d} \iint dz_0 dE_0 \chi_0 S_{in}(E_0) e^{-\mu_{CZT}(E_0)z_0} \mu_{CZT}(E_0)$$

where $S_0(E)$ is determined from the detected energy, E, which is defined as $$E = \nu_p(t_{TOF}^0 : z_0, E_0),$$

$S_{in}$ is the incident spectrum, $E_0$ is the incident energy, $z_0$ is an interaction point, n is an incident count rate, $\mu_{CZT}(E)$ is a linear attenuation value, $\tau_d$ is the dead time parameter, $\nu_p$ is an output voltage of a pre-amplifier; and $\chi_0$ is a probability of single photon events.

9. A method of performing pileup correction for a spectral computed-tomography scanner, the scanner including a photon-counting detector, the method comprising:
determining, using the method of claim 1, a parameter vector that includes a plurality of parameters of a detector pileup model of the photon-counting detector;
performing a scan using the scanner to generate a measured spectrum for the photon-counting detector; and
determining, using the detector pileup model and the measured spectrum, an incident spectrum for the photon-counting detector.

10. A device for determining a parameter vector that includes a plurality of parameters of a detector pileup model of a photon-counting detector, the detector pileup model being used for pileup correction for a spectral computed-tomography scanner, the device comprising:
a processor configured to
set values of the plurality of parameters, the plurality of parameters including a dead time parameter and individual probabilities of different pileup events, the individual probabilities including a probability of single photon events, a probability of double quasi-coincident photon events, and a probability of at least three quasi-coincident photon events;
determine, using (1) a detector response model, (2) an incident spectrum, and (3) the set values of the parameter vector, a plurality of component spectra, each component spectrum corresponding to one of the individual probabilities of the different pileup events;
sum the plurality of component spectra to generate an output spectrum;
calculate, based on the output spectrum and a measured spectrum, a value of a cost function;
update at least one of the values of the parameter vector; and
repeat the determining, summing, calculating, and updating steps until a stopping criteria is met, so as to determine a parameter vector that optimizes the cost function.

11. The device of claim 10, wherein the processor is further configured to set the dead time parameter based on the scanner geometry.

12. The device of claim 10, wherein the processor is further configured to
calculate the value of the cost function using:

$$\psi^2(\underline{a}) = \int dE [S_{out}(E, \underline{a}) - S_m(E)]^2$$

wherein $\psi(\underline{a})$ is the cost function, $\underline{a}$ is the parameter vector, $S_{out}(E, \underline{a})$ is the output spectrum, $S_m(E)$ is the measured spectrum, and E is energy.

13. The device of claim 10, wherein
the plurality of parameters further include a time threshold to distinguish between peak pileup events and tail pileup events; and the processor is further configured to determine, for the double quasi-coincident photon events, a peak pileup component spectrum and a tail pileup component spectrum.

14. The device of claim 10, wherein the processor is further configured to repeat the determining, summing, calculating, and updating steps until the cost function falls below a predetermined threshold or for a predetermined number of iterations.

15. The device of claim 10, wherein the processor is further configured to update the parameter vector a according to an exhaustive search method.

16. The device of claim 10, wherein the processor is further configured to update the parameter vector a according to a nonlinear least-squares method.

17. The device of claim 10, wherein the processor is further configured to determine, as one of the plurality of component spectra, a first component spectrum for single photon events, the first component spectrum being determined as:

$$S_0(E) = e^{-n\tau_d} \iint dz_0 dE_0 \chi_0 S_{in}(E_0) e^{-\mu_{CZT}(E_0)z_0} \mu_{CZT}(E_0)$$

where $S_0(E)$ is determined from the detected energy, E, which is defined as $$E = \nu_p(t_{TOF}^0 : z_0, E_0),$$

$S_{in}$ is the incident spectrum, $E_0$ is the incident energy, $z_0$ is an interaction point, n is an incident count rate, $\mu_{CZT}(E)$ is a linear attenuation value, $\tau_d$ is the dead time parameter, $\nu_p$ is an output voltage of a pre-amplifier; and $\chi_0$ is a probability of single photon events.

18. An apparatus for performing pileup correction for a spectral computed-tomography scanner, the scanner including a photon-counting detector, the apparatus comprising:
the device of claim 10,
wherein the processor is further configured to
cause the scanner to perform a scan to generate a measured spectrum for the photon-counting detector, and
determine, using the detector pileup model and the measured spectrum, an incident spectrum for the photon-counting detector.

19. A method for determining an output spectrum from a parameter vector that includes a plurality of parameters of a detector pileup model of a photon-counting detector, the detector pileup model being used for pileup correction for a spectral computed-tomography scanner, the method comprising:
setting values of the plurality of parameters, the plurality of parameters including a dead time parameter and individual probabilities of different pileup events, the individual probabilities including a probability of single photon events and a probability of double quasi-coincident photon events;
determining, using (1) a detector response model, (2) an incident spectrum, and (3) the set values of the parameter vector, a plurality of component spectra, each component spectrum corresponding to one of the individual probabilities of the different pileup events, wherein the determining step includes determining, as one of the plurality of component spectra, a first component spectrum for single photon events, the first component spectrum being determined as:

$$S_0(E) = e^{-n\tau_d} \iint dz_0 dE_0 \chi_0 S_{in}(E_0) e^{-\mu_{CZT}(E_0)z_0} \mu_{CZT}(E_0)$$

where $S_0(E)$ is determined from the detected energy, E, which is defined as $$E = \nu_p(t_{TOF}^0 : z_0, E_0),$$

$S_{in}$ is the incident spectrum, $E_0$ is the incident energy, $z_0$ is an interaction point, n is an incident count rate, $\mu_{CZT}(E)$ is a linear attenuation value, $\tau_d$ is the dead time parameter, $v_p$ is an output voltage of a pre-amplifier; and $\chi_0$ is a probability of single photon events; and summing the plurality of component spectra to generate the output spectrum.

\* \* \* \* \*